(12) United States Patent
Xu et al.

(10) Patent No.: US 7,651,762 B2
(45) Date of Patent: Jan. 26, 2010

(54) METHODS AND DEVICES USING A SHRINKABLE SUPPORT FOR POROUS MONOLITHIC MATERIALS

(75) Inventors: Dengfeng Xu, Irvine, CA (US); Robert Lee Grenz, Santa Ana, CA (US)

(73) Assignee: Varian, Inc., Palo Alto, CA (US)

(*) Notice: Subject to any disclaimer, the term of this patent is extended or adjusted under 35 U.S.C. 154(b) by 351 days.

(21) Appl. No.: 11/717,317

(22) Filed: Mar. 13, 2007

(65) Prior Publication Data
US 2008/0223786 A1    Sep. 18, 2008

(51) Int. Cl.
*B32B 3/26* (2006.01)
*B01D 15/08* (2006.01)
*B29C 35/00* (2006.01)

(52) U.S. Cl. .................. 428/304.4; 428/67; 428/312.2; 428/312.8; 428/318.4; 428/319.1; 210/656; 210/198.2; 264/414

(58) Field of Classification Search ........................ None
See application file for complete search history.

(56) References Cited

U.S. PATENT DOCUMENTS

| | | | |
|---|---|---|---|
| 3,480,616 A | 11/1969 | Osipow et al. | |
| 4,375,163 A | * 3/1983 | Yang | .................. 73/61.53 |
| 5,009,688 A | 4/1991 | Nakanishi | |
| 5,023,208 A | 6/1991 | Pope et al. | |
| 5,100,841 A | 3/1992 | Wada et al. | |
| 5,624,875 A | 4/1997 | Nakanishi et al. | |
| 5,922,099 A | 7/1999 | Yoon et al. | |
| 6,080,339 A | 6/2000 | Fleming et al. | |
| 6,207,098 B1 | 3/2001 | Nakanishi et al. | |
| 6,210,570 B1 | 4/2001 | Holloway | |
| 6,398,962 B1 | 6/2002 | Cabrera et al. | |
| 6,531,060 B1 | 3/2003 | Nakanishi et al. | |
| 6,541,539 B1 | 4/2003 | Yang et al. | |
| 6,562,744 B1 | 5/2003 | Nakanishi et al. | |
| 6,592,764 B1 | 7/2003 | Stucky et al. | |
| 6,620,368 B1 | 9/2003 | Wang et al. | |

(Continued)

FOREIGN PATENT DOCUMENTS

WO    WO 2005/072164 A    8/2005

OTHER PUBLICATIONS

Article by Mikhail, et al. entitled "Investigations of a Complete Pore Structure Analysis", published by Journal of Colloid and Interface Science, 26,45-53, (1968).

*Primary Examiner*—Ling Xu
(74) *Attorney, Agent, or Firm*—Cynthia R. Moore; Bella Fishman

(57) ABSTRACT

Articles of manufacture and devices and methods of forming and using the same are provided, wherein the article comprises a porous inorganic substrate contained in or bounded by a support made from an inorganic material are provided, wherein said porous substrate and support are heated to a temperature effective to shrink the support onto the porous substrate such that liquid tight contact is formed between the porous substrate and the support. In a preferred aspect, the porous inorganic substrate has a porosity of at least 5%, and is a porous monolith formed using a sol-gel method. The articles thus formed provide a confined fluid flow through the porous substrate, providing superior performance in separations, catalysis, filtration, and the like.

24 Claims, 5 Drawing Sheets

A

B

U.S. PATENT DOCUMENTS

| | | |
|---|---|---|
| 6,783,680 B2 | 8/2004 | Malik |
| 6,797,174 B2 | 9/2004 | Neuroth et al. |
| 6,884,822 B2 | 4/2005 | Wang et al. |
| 7,026,362 B2 | 4/2006 | Wang et al. |
| 7,125,488 B2 | 10/2006 | Li |
| 7,125,912 B2 | 10/2006 | Wang et al. |
| 2003/0148053 A1 | 8/2003 | Wang et al. |
| 2003/0150811 A1 | 8/2003 | Walter et al. |
| 2003/0213732 A1 | 11/2003 | Malik et al. |
| 2003/0230524 A1 | 12/2003 | Soga et al. |
| 2006/0131238 A1 | 6/2006 | Xu |

* cited by examiner

A

B

METHODS AND DEVICES USING A SHRINKABLE SUPPORT FOR POROUS MONOLITHIC MATERIALS

FIELD OF THE INVENTION

This invention relates generally to components useful in analytical or preparative applications and chemical processing or catalysis, and methods of preparing and using the same.

BACKGROUND OF THE INVENTION

Porous monolithic materials are used in a variety of applications such as filtration, adsorption and catalysis, among others. Such materials are often mounted in and contained in intimate contact with a supporting structure such as a containing tube, which both supports and protects the porous medium, and for some applications, confines the flow of a liquid or gas. For proper function of a particular process, it can be important to confine the fluid (or gas) flow through the porous monolith and to minimize flow around the porous monolith, which may occur when the fluid flows in gaps present between the porous monolith and its supporting structure. Leakage through gaps between the porous monolith and its supporting structure can result in insufficient or poorly controlled contact between the porous material and the fluid (or gas) and any components present therein, diffusion broadening of chromatographic peaks, inadequate adsorption or catalysis, etc. In order to avoid these problems, it is necessary to provide a liquid or gas tight contact between the edges of the porous monolith and its supporting structure so that contact between the fluid and its components with the porous monolith can be controlled as desired.

Depending on the application and the choice of specific materials appropriate to that application, a variety of assembly processes may be used to make structures that are suitable for applications which include a porous monolith associated with a support structure. However, many of these structures suffer from excessive leakage around the edges due to shrinkage of the porous monolith away from its associated support. For example, inorganic materials such as glass or ceramic are frequently used for their resistance to solvents and high-temperature. The manufacture of structures using these materials frequently requires the use of high-temperature processing steps. For this and other reasons, there is often significant shrinkage of the porous material during manufacture. The use of a rigid support material may result in the appearance of excessive gaps at the inside wall after the completion of all manufacturing steps, and cause the porous material to be unsecured with respect to its supporting structure.

One solution to these problems is to provide a shrinkable support that can contract to provide close contact with the contained or associated porous monolithic material. Shrinkable polymers are well-known and widely-used. In sheet form, they are used in vacuum forming and in "shrink-wrapping." In tube form, they are frequently used to form a protective, insulating and/or supportive outer layer of near-cylindrical parts, especially for electrical applications. However, such polymer materials cannot be used in many applications, because the thermal and/or chemical resistance of the material is not compatible with the application.

A common technique in precision metal fabrication is to make an outer part with an inner dimension just slightly smaller than the outer dimension of an inner part. By heating the outer part, its dimensions can be expanded just enough to allow insertion of the inner part. On cooling, the two parts have an "interference" fit which provides intimate contact without leakage and a firm connection without a bonding agent. However, such techniques are only suitable if the dimensions of the two parts to be assembled can be held to extremely tight tolerances, which may not be possible with porous monolithic materials.

Similar techniques are used to create electrical or other metallic feedthroughs in the glass walls of vacuum tubes, light bulbs and the like. Metal rods or wires are inserted through holes or glass tubes. The glass is heated until it softens and the holes or gaps shrink around the metal to form a vacuum-tight seal. Thus, although using glass as a shrinkable medium to provide sealing against metal parts is known in the art, it has not been used with porous monolithic materials to provide sealing between the containing or supporting walls and the porous monolith. In contrast, glass has been used as a container and mold for producing porous monoliths formed by sol gels, but upon drying and calcination, the porous monolith becomes loose in the support. This problem has not been solved.

Sol-gel processing of glasses has been used for the manufacture of optical fibers having an overcladding tube. For example, U.S. Pat. No. 5,922,099 to Yoon, et al. and U.S. Patent Application Publication No. 2003/0148053 to Wang, et al. describe casting sol-gel materials into a tubular mold to form the overcladding tube for an optical fiber and a sol-gel-derived rod, comprising a cylindrical core portion and a tubular cladding portion around and concentric with the core portion. U.S. Pat. No. 6,080,339 to Fleming et al. describes an extrusion process to extrude sol-gel material for the purpose of making overcladding tubes, substrate tubes, and optical fibers themselves. The extruded tubes are then subjected to the usual processing conditions, including heating for preparation of optical fibers. However, these references do not describe methods for providing a porous monolithic core having liquid tight contact between the porous monolith and the containing walls that is suitable for use in analytical or preparative devices, or the like. In fact, the processes utilized in manufacture of optical fibers would be incompatible with retention of porosity in porous monolithic materials, as the presence of pores would reduce the optical clarity and transmittance of the fibers, and therefore, is an undesirable feature in optical fibers.

Sol-gel processing to form a porous monolith inside capillaries is also known. However, the fused silica capillaries have a very high melting temperature, and heating the capillary and porous monolith to a sufficiently high temperature to shrink the capillary down to maintain contact with the porous monolith as it forms and is further processed (e.g., dried and calcined) would destroy the porosity of the monolith, just as in the case of preparation of optical fibers. Therefore, alternative solutions have been sought. For example, U.S. Pat. No. 6,562,744 to Nakanishi et al. describes a process for making capillary chromatographic columns wherein the porous material inside the capillary is allegedly in liquid tight contact with the capillary by virtue of an affinity of the capillary walls for the gelling silicate components in the porous material. This patent also describes using a shrinkable PTFE capillary to form a liquid tight contact between the porous material and the capillary. However, PTFE does not provide sufficient support for fragile porous monoliths formed by sol gel methods, and cannot be heated to a temperature sufficient to calcine the sol gel monolith and remove organic contaminants. Further, the patent teaches that special treatments of the capillary inner surface are required.

U.S. Pat. No. 6,531,060 to Nakanishi et al. describes a similar process for forming a porous monolith inside a fused silica capillary. U.S. Patent Application Publication No.

2003/0213732 to Malik et al. also describes chemical anchorage of the monolith to the capillary walls. In addition, U.S. Pat. No. 6,783,680 to Malik describes the preparation of a sol-gel stationary phase formed inside fused silica capillary tubing and reports that the sol gel is chemically bonded to the capillary walls as a result of condensation reaction with the silanol groups on the capillary inner surface. The capillary can be further treated with heat up to 350° C. However, the above described techniques are only useful when working with small dimensions such as exist in capillary tubing, in which diameters are generally less than 1 mm and typically less than 0.1 mm. For example, the largest diameter fused silica capillary tubing utilized by Malik was only 0.25 mm in diameter, and such small diameters limit the applications and utility of the method.

Another difficulty encountered in minimizing leakage or gaps between a porous monolith and its containing structure, especially when prepared using sol-gel methods, is that processing introduces shrinkage or cracking during the drying step of the fabrication process. Approaches to reduce the cracking have been attempted, focused on increasing the pore sizes of the monolith to reduce the capillary stresses generated during drying. For example, U.S. Pat. No. 5,023,208 to Pope describes subjecting the gel to a hydrothermal aging treatment, which reportedly causes silica particles to migrate and fill small pores in the porous gel matrix, and increase the average pore size. U.S. Pat. No. 6,620,368 to Wang describes that the density of the gel at the end of the first stage of liquid removal process corresponds to a shrinkage in the linear dimension of between about 15% and 35%. However, these additional processing steps are time consuming and the products are expensive to manufacture.

U.S. Pat. No. 6,210,570 to Holloway describes a method for preparing a chromatography column containing a hydrosol with minimal shrinkage, wherein the hydrosol has a first volume, and after being induced to produce a monolith has a second volume that is at least about 95% of the first volume. The hydrosol is described as having a $SiO_2$ concentration of less than about 5 g/ml, or between about 3 g/ml and about 5 g/ml. The patent further states that a balance should be achieved between syneresis prevention and producing a brittle silica product due to too low a $SiO_2$ concentration. This reduction in "syneresis," or the shrinkage in volume as a hydrosol progresses to a hydrogel, is reported to avoid the resolution problems caused when mobile phase effectively bypasses portions of the stationary phase, resulting in poor separation of components during chromatographic separation. However, these processes for producing a porous monolith with reduced shrinkage sacrifice control of the gel composition, porosity and pore size distribution, and the porous monolithic materials produced lack in mechanical strength.

Accordingly, there remains a need for a shrinkable support material that can be applied to the exterior surface of porous monolithic materials to minimize gaps, provide more intimate contact and reduce leakage.

SUMMARY OF THE INVENTION

Accordingly, it is a primary object of the invention to address the aforementioned needs in the art by providing an inorganic shrinkable support that can be applied to the exterior surface of porous materials used for chromatography, filtration, purification, catalysis, and the like. Methods for fabricating structures using such materials are also required.

Accordingly, there is provided an article of manufacture or a device (or a component of an article of manufacture or device) comprising a porous inorganic substrate contained in or bounded by a support made from an inorganic material ("a supported porous substrate"), wherein said porous substrate and support are heated to a temperature effective to shrink the support onto the porous substrate such that liquid tight contact is formed between the porous substrate and the support. The article thus provides a confined fluid flow through the porous substrate, and the fluid flow is not allowed to bypass the porous substrate, providing superior performance in separation, catalysis, filtration, and the like.

Preferably, the porous inorganic substrate has a total porosity of at least 5%. In certain embodiments, the porous substrate is characterized by a total porosity of at least 60% and in certain additional embodiments, the porous substrate is characterized by a total porosity of from about 85% to about 97%. In certain embodiments, the porous substrate is characterized by a mesopore mode distribution of about 2 nm to about 100 nm, and in other embodiments, the porous substrate is characterized by a mesopore mode distribution of about 8 nm to about 50 nm, and a mesopore volume of at least about 0.2 cc/g, more preferably at least about 0.5 cc/g. In particularly preferred embodiments, the porous inorganic substrate is a porous monolith comprising an inorganic material and having a total porosity of at least 5% (a "supported porous monolith"). In certain embodiments, the porous monolith is characterized by a mesopore mode distribution of about 2 nm to about 100 nm, and in other embodiments, the porous monolith is characterized by a mesopore mode distribution of about 8 nm to about 50 nm, and a mesopore volume of at least about 0.2 cc/g, more preferably at least about 0.5 cc/g. However, the porosity and specific pore characteristics of the porous inorganic substrate are not limited, and can be chosen to suit particular applications.

In particular embodiments, the temperature that is effective to shrink the support onto the porous inorganic substrate is a temperature that is effective to soften the support (e.g., the softening temperature) allowing the support to shrink to form a liquid tight contact with the porous inorganic substrate. Preferably, the temperature effective to shrink the support onto the porous monolith has no affect on the pore distribution of the porous monolith. In particular embodiments, the temperature that is effective to shrink the support onto the porous monolith is less than about 2000° C., and more preferably is less than about 1000° C.

In a particular embodiment, a vacuum is applied to the interior of the support (e.g., an unheated end), wherein the application of vacuum results in a decrease in the temperature at which shrinkage occurs. By appropriate choice of porous inorganic substrate (choice of monolithic or nonmonolithic substrate, optionally having a desired composition, porosity and/or pore characteristics), and support (having a particular softening temperature), and performing the shrinkage step in the appropriate conditions (e.g., with or without a vacuum applied to the support), an article or device can be obtained having desired porosity and/or pore characteristics and a liquid tight contact between the porous substrate and the support.

In certain embodiments, the porous inorganic substrate and support are initially separated by a gap, and upon heating to a temperature effective to soften the support, the support shrinks onto the porous inorganic substrate so that the gap is minimized and the porous substrate and the support are in liquid tight contact. In additional embodiments, the porous inorganic substrate is formed in the support without a gap being present between them (e.g., a sol gel monolith is formed), and subsequent heating is performed to shrink the support either simultaneously with the shrinking of the porous monolith as it is calcined, or after the porous monolith is calcined, such that there is no gap between them at least upon reaching the final treatment temperature. In some embodiments, there is no gap between them at any stage in the process. In other embodiments, a vacuum is applied to the support that is sufficient to lower the temperature at which shrinkage occurs.

In certain preferred embodiments, the porous inorganic substrate and the support have a cylindrical shape. In particular embodiments, the support has an internal diameter greater than about 1 mm. In additional embodiments, the support has an internal diameter less than about 1 mm. In particularly preferred embodiments, the article is adapted for use in chromatography, catalysis, adsorption, filtration, fuel cells, optoelectronics, sensor technologies, or hydrogen storage, and most preferably chromatography as a chromatography column In certain aspects, the porous inorganic substrate comprises an inorganic material or an inorganic-organic hybrid material, and in particular embodiments, the inorganic material comprises a glass or ceramic material. Preferably, the inorganic material comprises a metal or metalloid oxide, preferably selected from oxides of Si, Ge, Sn, Al, Ga, Mg, Mb, Co, Ni, Ga, Be, Y, La, Pb, V, Nb, Ti, Zr, Ta, W, Hf, or combinations thereof.

In a preferred aspect, the porous inorganic substrate is a porous monolith formed using a sol-gel method using one or more sol gel precursors having hydroxyl or hydrolyzable ligands that are capable of undergoing a sol gel reaction to form a sol gel. Suitable hydrolyzable ligands include, but are not limited to, halogen, alkoxy, amino or acyloxy. In particular embodiments, the sol gel precursor can further comprise an organic substituent, and can include an organosilane, for example, such as an alkoxy-, halo-, acyloxy- or amino silane, further comprising an organic substituent, such as a saturated or unsaturated hydrocarbyl substituent, aryl substituent, or mixtures thereof. Typical alkoxysilanes can include, for example, alkyltrialkoxysilane, cycloalkyltrialkoxysilane, dialkyldialkoxysilane, trialkylalkoxysilane, tetraalkoxysilane, vinyltrialkoxysilane, allyltrialkoxysilane, phenylalkyldialkoxysilane, diphenylalkoxysilane, or naphthyltrialkoxysilane, or mixtures thereof. The sol gel precursor comprising an organic substituent can also include other organometallic compounds such as organogermanes, or organosubstituted titanium, aluminum, zirconium or vanadium alkoxides, and the like. In another preferred embodiment, the silane is a mixture of silanes comprising a trialkoxysilane and a tetraalkoxysilane. In alternative embodiments, the porous monolith is formed from particles that are modified to form a monolith.

In particular embodiments, the porosity, chemistry, adsorption or catalytic characteristics of the porous monolith are modified by the introduction of a bonded phase (e.g., via reaction with an organosilane or endcapping reagent), introduction of a catalytic functionality (e.g., platinum, protein such as an enzyme, nucleic acid such as a ribozyme), structure remodeling (e.g., using a matrix dissolving catalyst, or hydrothermal treatment), or introduction of a sensor (e.g., a dye or enzyme), but is not limited to these applications. Alternatively, the porous monolith can be formed using components that provide the modified features providing catalytic functionality, a bonded phase, structure remodeling or sensors, and the like.

In particular embodiments, the support is made from an inorganic material comprising a glass or ceramic material. Preferably, the support is non-porous. In particular embodiments, the support is formed using a sol-gel process.

In certain aspects, the article further comprises an outer polymer layer, and can be provided with threaded ends. Preferably the outer polymer layer is a liquid crystal polymer, thermoplastic polymer resin or a thermoset polymer resin. In particular embodiments, the outer polymer coating is polyarylether ether ketone (PEEK).

In additional embodiments, methods are provided for forming an article comprising a porous inorganic substrate in liquid tight contact with an inorganic support comprising: a) assembling a porous inorganic substrate into a shrinkable support comprising an inorganic material, and b) shrinking the support onto the porous inorganic substrate by heating the article to a temperature that is effective to shrink the support onto the porous inorganic substrate such that there is liquid tight contact between the porous substrate and the support.

In certain aspects, the porous inorganic substrate comprises an inorganic material or an inorganic-organic hybrid material, and in particular embodiments, the inorganic material comprises a glass or ceramic material. Preferably, the inorganic material comprises a metal or metalloid oxide, preferably selected from oxides of Si, Ge, Sn, Al, Ga, Mg, Mb, Co, Ni, Ga, Be, Y, La, Pb, V, Nb, Ti, Zr, Ta, W, Hf, or combinations thereof.

In a preferred aspect, the porous inorganic substrate is a porous monolith formed using a sol-gel method using one or more sol gel precursors having hydroxyl or hydrolyzable ligands that are capable of undergoing a sol gel reaction to form a sol gel. Suitable hydrolyzable ligands include, but are not limited to, halogen, alkoxy, amino or acyloxy. In particular embodiments, the sol gel precursor can further comprise an organic substituent, and can include an organosilane, for example, such as an alkoxy-, halo-, acyloxy- or amino silane, further comprising an organic substituent, such as a saturated or unsaturated hydrocarbyl substituent, aryl substituent, or mixtures thereof. In alternative embodiments, the porous monolith is formed from particles that are modified to form a monolith.

Preferably, the article is a chromatography column comprising an inorganic porous monolithic stationary phase contained in a support made from an inorganic material, and the method of manufacturing the chromatography column provides liquid tight contact between the porous inorganic monolith and the support. When utilized in the preparation of chromatographic columns, preferably the method provides a column exhibiting increased chromatographic efficiency and improved separation, peak shape, peak height, and the like, as well as ease and reduced cost of manufacture with respect to prior art methods that do not provide a liquid tight contact between the porous inorganic substrate and the support.

In particular embodiments, the porous monolith is formed separately from said shrinkable support and inserted therein prior to shrinking. In additional embodiments, the porous monolith is formed inside said shrinkable support prior to shrinking.

Preferably, the shrinkable support is formed from an inorganic material such as a glass or ceramic. In particular embodiments, the shrinkable support is made by a sol-gel process.

In particular embodiments, the article is adapted for use in chromatography, catalysis, adsorption, separation, filtration, fuel cells, optoelectronics, sensor technologies, or hydrogen storage, more preferably chromatography. In certain embodiments, the method further comprises providing an outer protective layer comprising glass, metal, or polymer, or combinations thereof. The outer layer of polymer can be applied by any method known in the art, such as a coating, shrinking, extrusion or an overmolding process. In preferred embodiments, the article is used for chromatography, filtration or purification, catalysis, environmental or medical sensing, production of energy in fuel cells, hydrogen storage, or optical switching in optoelectronics devices.

In a particularly preferred embodiments, there is provided a chromatographic column comprising a porous monolith enclosed inside a glass tubing, the improvement comprising forming the porous monolith from a sol gel and assembling it into the glass tubing, and heating the assembly to calcine the sol gel and shrink the glass tubing such that there is liquid tight contact between the porous monolith and the glass tubing. In particular embodiments, the porous monolith is formed and calcined inside the glass tubing. In certain embodiments, the heating is performed in a plurality of stages to dry the sol gel, to calcine the sol gel and to shrink the glass tubing. In additional embodiments, the heating is performed in a single temperature programmed step.

In an additional aspect, there is provided a method for separating a mixture of analytes in a sample, said method comprising the steps of a) providing a chromatographic column comprising a porous monolith enclosed inside a glass tubing, wherein the column has been heated to shrink the glass tubing such that there is liquid tight contact between the porous monolith and the glass tubing; b) applying the sample to the chromatographic column; c) eluting the chromatographic column with a mobile phase; and d) collecting the separated analytes eluting from the chromatographic column.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

I. Definitions and Overview

Figure 1:
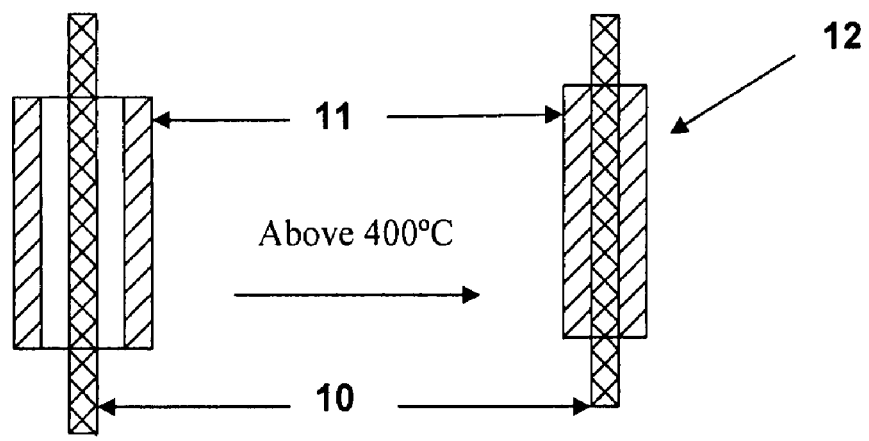
FIG. 1 shows one embodiment of the invention in which a porous monolithic rod is inserted into a shrinkable tube and is heated to shrink the tube onto the rod.
Figure 1:
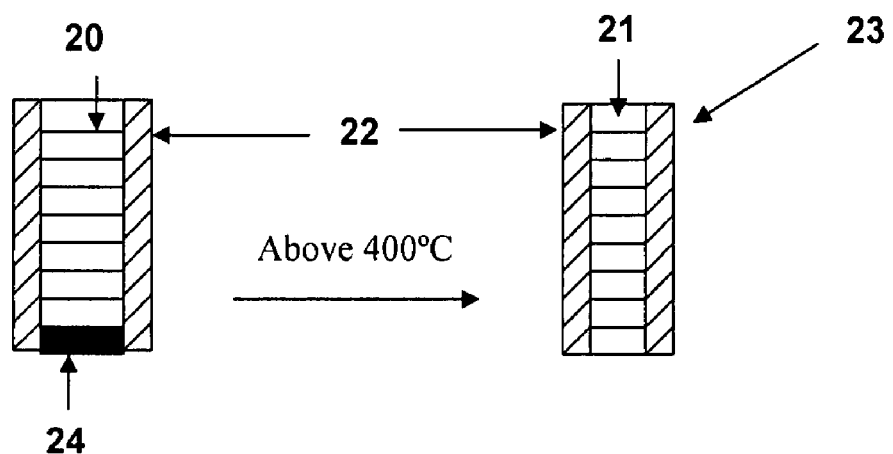

Before the present invention is described in detail, it is to be understood that unless otherwise indicated this invention is not limited to specific inorganic substrates, sol-gel formulations, glasses, porous media, surface treatments, chromatographic methods, filtration and purification structures, catalytic structures, or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "a metal oxide" includes two or more metal oxides; reference to "a support" includes two or more supports, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "porosity" refers to the proportion of the volume of the porous inorganic substrate that is open, that is, unoccupied by solid material, and can include the proportion of the volume that is occupied by gases (e.g., nitrogen or air or gaseous mobile phase) or liquids (e.g., liquid mobile phase). Typically, the porosity is at least 5%, but any porosity can be chosen to suit a particular application.

As used herein, the term "macropores" refers to pores with diameters greater than about 0.05 μm (50 nm, or 500 Å); the term "mesopores" refers to pores with diameters between about 2 nm and 50 nm (20 Å-500 Å); and the term "micropores" refers to pores with diameters less than about 2.0 nm (20 Å).

As used herein, the term "total pore volume" refers to the total volume of the pores in the monolith, and is usually expressed in $cm^3/g$, or cc/g. The total pore volume can be measured by mercury intrusion, where Hg is pumped into the pores under high pressure.

The term "BET surface area" refers to the determination of surface area using the BET method, which can be determined using either a single point or multiple point analysis. For example, multipoint nitrogen sorption measurements can be made on a Micromeritics TriStar 3000 instrument (Norcross, Ga.). The specific surface area can then be calculated using the multipoint BET method, and the mode pore diameter is the most frequent diameter from the log differential pore volume distribution (dV/d log(D) vs. D). The mesopore volume is calculated as the single point total pore volume at $P/P_0=0.98$.

The term "monolith" refers to a porous, three-dimensional material having a continuous interconnected pore structure in a single piece, as opposed to a collection of discrete particles packed into a volume.

As used herein, the term "liquid tight contact" refers to the condition where the support has shrunk into contact with the porous inorganic substrate such that fluid flow is confined through the porous inorganic substrate by the support, and the fluid does not substantially flow between the porous inorganic substrate and the support. Liquid tight contact also encompasses gas tight contact. Liquid tight contact can also encompass chemical bonding between the support and substrate (e.g., silanol condensation) that can form once the porous substrate and support are in close contact. For example, when adapted for use in chromatography, liquid tight contact can be demonstrated by the separation of analytes and the appearance of symmetrical peak shapes. Leakage of mobile phase between the porous inorganic substrate and the support would result in poor or no separation of analytes and poor peak shapes. The superior separation and peak shapes obtained in Example 4 thus demonstrate the liquid tight contact achievable using the present methods.

The present invention is related to unique articles and methods of forming them, such as chromatographic columns, filters, catalytic structures, optical devices (such as waveguides), fuel cells, hydrogen storage devices, and the like, wherein liquid tight contact is provided between a porous inorganic substrate and a nonporous inorganic supporting structure. The present inventors have surprisingly discovered that a shrinkable inorganic material can be heated to cause it to shrink or contract into liquid tight contact with the exterior surface of a porous substrate, resulting in superior properties and performance. Although practitioners have been extensively employing these materials in the preparation of chromatography columns and similar apparatus, the present inventors are the first to discover that an inorganic support can be heated to shrink it into liquid tight contact with the exterior surface of a porous substrate such as a porous glass monolith, and to utilize this property to produce products having superior performance, ease of use and manufacture, to the inventors' knowledge to date.

Accordingly, there is provided a supported porous substrate comprising a porous inorganic substrate contained in or bounded by a support made from an inorganic material, wherein said porous substrate and support are heated to a temperature effective to shrink the support onto the porous substrate such that there is liquid tight contact between the porous monolith and the support. The article thus provides a confined fluid flow through the porous substrate, and the fluid flow is not allowed to bypass the porous substrate, providing superior performance in separation, catalysis, filtration and the like. Preferably, the porous inorganic substrate is a porous monolith, thereby providing a supported porous monolith.

The methods described are particularly useful when used with high porosity structures, substrates that are fragile or sensitive to environmental conditions of use, applications which use corrosive solvents or gases, applications which operate at high temperature, and indeed any application where glass or ceramic materials are preferred, and edge leakage is not acceptable.

The devices and methods described herein are particularly useful for applications wherein confining fluid flow through a porous bed, particularly a monolithic bed, is advantageous because the close contact between the porous substrate and the supporting structure does not allow fluid to flow between the two, i.e., there is liquid tight contact between them.

Such structures may be of any size or shape to suit the need of any specific application. For example, for chromatographic applications, the structure may be in the form of capillary tubes of narrow diameter (e.g., 10 μm–1 mm I.D.), which can be especially useful in analytical applications, while for chromatographic preparative applications, the structure can be larger, such as tubes of large diameter (e.g., greater than 1 mm ID and up to 6 inches or greater). Theoretically, there is no limitation in size, and the dimensions of the devices can be determined entirely from the constraints of practical applications. For some applications, much larger diameter tubes might be used, and non-tubular structures may also be used. Smaller structures may also be contemplated for micro-fabricated devices. The present invention can be applied to make parts in any relevant size range requiring only sufficient material and processing equipment of sufficient size to handle the parts to be processed.

Materials for both the porous substrate and the shrinkable support can be selected from a range of commercially-available sources or custom-fabricated to suit. For example, the inorganic porous substrate can include inorganic chromatographic media, filter media, fuel cell compositions, sensors and sensor arrays, optoelectronic devices, hydrogen storage media or catalytic support media, optionally along with any surface treatment suitable to facilitate particular analytical measurements, chemical processes, adsorption processes, optical properties, and the like. The porous inorganic substrate can serve as a controlled porosity medium for use with liquid or gas flow, it may serve to mechanically filter particles of a particular size, or it may serve as a large-surface-area reaction or adsorption surface for purification, catalytic reactions, energy production, and the like.

Similarly, the shrinkable support can be fabricated from any suitable material which can be made to shrink or contract upon heating and which does not damage the porous inorganic substrate. For example, any glass or ceramic materials or metals may be suitable as long as they soften and shrink sufficiently at an acceptable processing temperature. In a particular embodiment, glass or ceramic tubing made by sol-gel casting or extrusion is used. Furthermore, the support may itself be porous if such is useful to a particular application. In preferred embodiments, the glass or ceramic tubing can be of conventional extruded or pulled manufacture.

Generally, two basic methods can be used to assemble the porous substrate into liquid tight contact with the support substrate. Referring to FIG. 1A, in one embodiment, a porous inorganic substrate, the porous monolith 10, can first be prepared using a suitable method. It can then be inserted into an opening in a shrinkable support 11. Heat is supplied to the assembly so that support 11 shrinks to provide liquid tight contact against the porous monolith 10 to produce form 12 having liquid tight contact between the support and the porous monolith.

Referring to FIG. 1B, in another embodiment, the porous inorganic substrate can be prepared in situ by filling a containing support 22 with a suitable precursor material 20. In a preferred embodiment, said precursor material is a sol-gel held in the support by a seal 24, which is allowed to dry in situ or can be heated to hasten drying, or both. Heat applied to the assembly can further transform the porous inorganic substrate into a monolithic dry gel 21 if not previously dried. Additional heating to a calcining temperature can further calcine the porous monolith if desired. Heating also serves to shrink the support to its finished structure 23 in liquid tight contact with the porous monolith. The temperature ranges and times over which desired changes occur can readily be adjusted so that the porous monolith has finished drying and shrinking before the support substrate has shrunk to its final size.

In particular embodiments, the porous substrate can be a porous solid that is not monolithic. For example, the porous substrate 10 could be formed from compressed porous particles. The support can be shrunk into liquid tight contact with support 11 as described in FIG. 1A.

The basic process illustrated in FIG. 1B can also be utilized with a non-monolithic porous medium. The support 22 can be filled with particles such as a powder or beads that can be further modified by surface reactions or by sintering so that the particles agglomerate or coalesce and the particulate porous substrate becomes monolithic. A combination of the above steps can also be utilized.

In any of these embodiments, a vacuum can be applied to the interior of the support, causing the support to shrink onto the porous inorganic substrate at a lower temperature than would be required in the absence of a vacuum. For example, application of a vacuum of about 20 inches of mercury can be provided to lower the softening temperature required for shrinking by about 100 to 150° C. In view of the present disclosure, one skilled in the art can readily envision that appropriate choice of softening temperature for the support and calcining or sintering temperature for the porous monolith can be made under conditions with or without applied vacuum.

In any of the above embodiments, surface modification may be performed as appropriate, either before or after shrinkage of the support. For example, a bonded phase can be introduced to the porous inorganic substrate, or a porous inorganic substrate can be endcapped to reduce residual silanols. Generally, introduction of any organic moieties is performed after the shrinkage step has been performed in order to avoid heating. Surface preparations and introduction of a polar bonded phase can also be preformed at this stage, for example, as described in U.S. Pat. No. 7,125,488 to Li.

Further, to provide protection and/or facilitate assembly of the finished article into an apparatus, an additional optional outer protective layer or coating (e.g., a glass, metal or polymer layer) may be applied by coating, casting, overmolding or other means. Preferably the outer polymer layer is a liquid crystal polymer, thermoplastic polymer resin or a thermoset polymer resin. In particular embodiments, the outer polymer coating is polyarylether ether ketone (PEEK). The outer polymer coating can be utilized to provide the article with a configuration to facilitate assembly into an apparatus for any desired applications, such as threaded ends, or flow adaptors, and the like.

Figure 2:
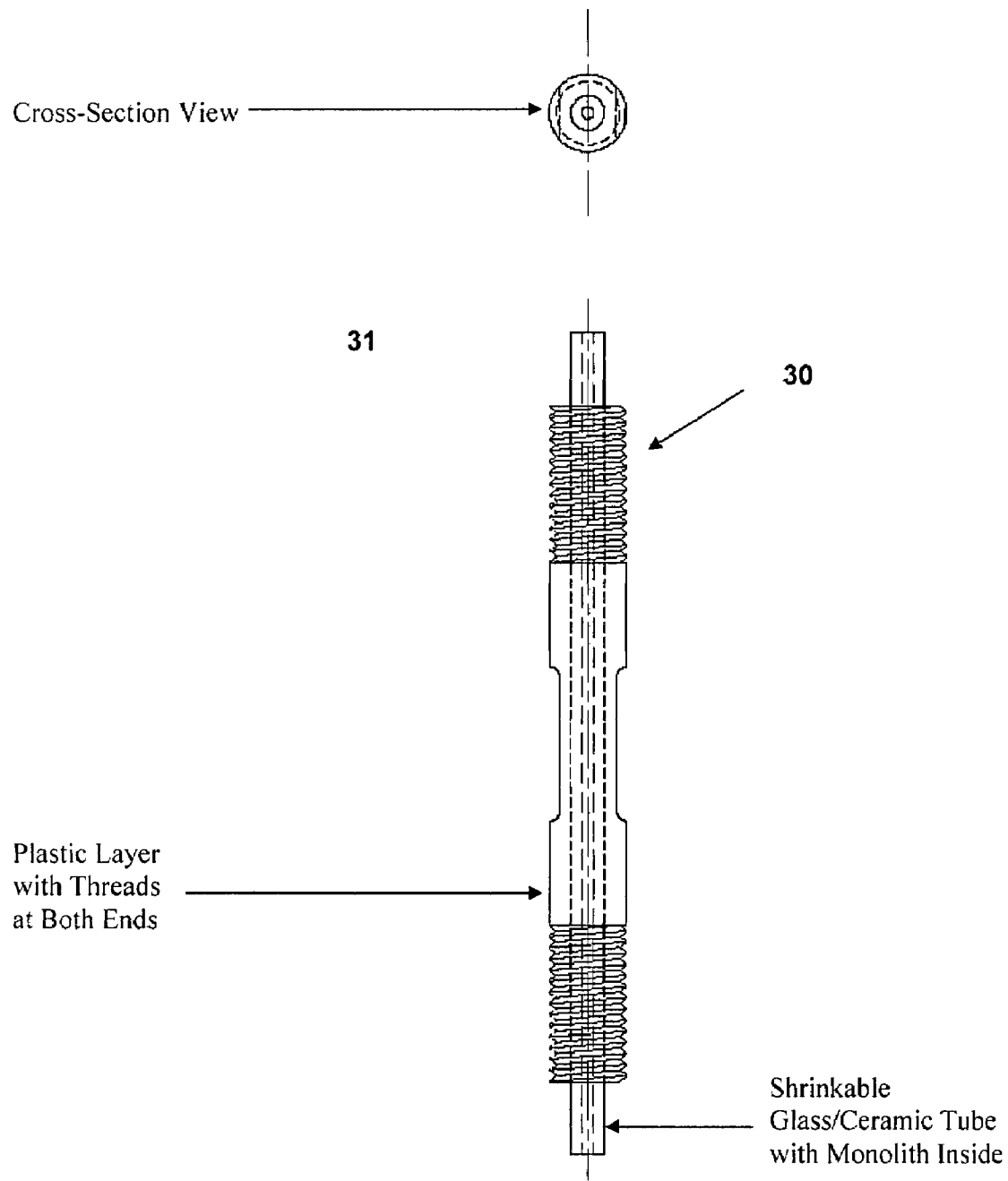
FIG. 2 shows a second embodiment of the invention in which a porous monolith is formed using a sol gel process in a shrinkable tube and the porous monolith and tube are heated together to calcine the rod and to shrink the tube onto the rod.

As shown in FIG. 2, a thermoplastic resin layer with threaded ends 30 can be overmolded onto the supported porous substrate to form a chromatography column 31. A cross sectional view shows a shrinkable glass or ceramic tube including a porous monolith inside the outer thermoplastic resin layer. In other embodiments, a plastic or rubber coating could be applied by dipping, spraying, or heat shrinking. Similarly other materials can be assembled onto the finished supported substrate by wrapping around the article or insertion or other means.

Figure 3A:
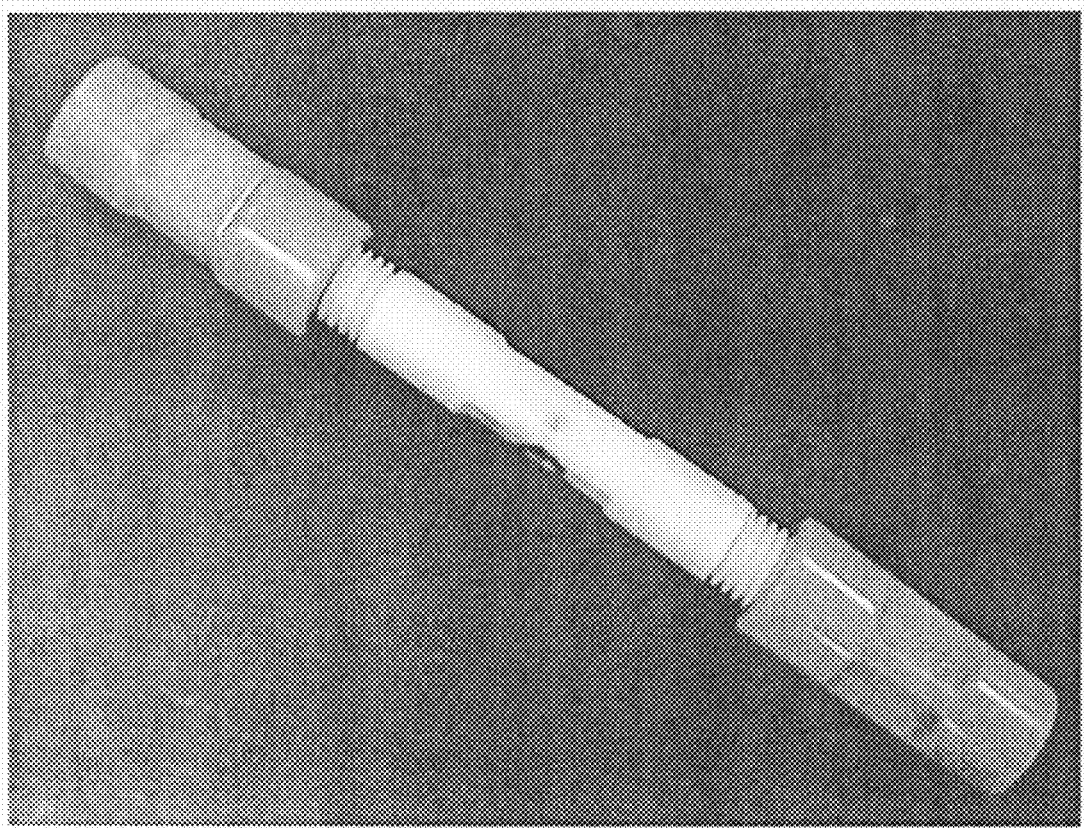
FIG. 3A shows an embodiment of the invention adapted for chromatography showing a thermoplastic overcladding provided with threaded mounts at each end.
Figure 3B:
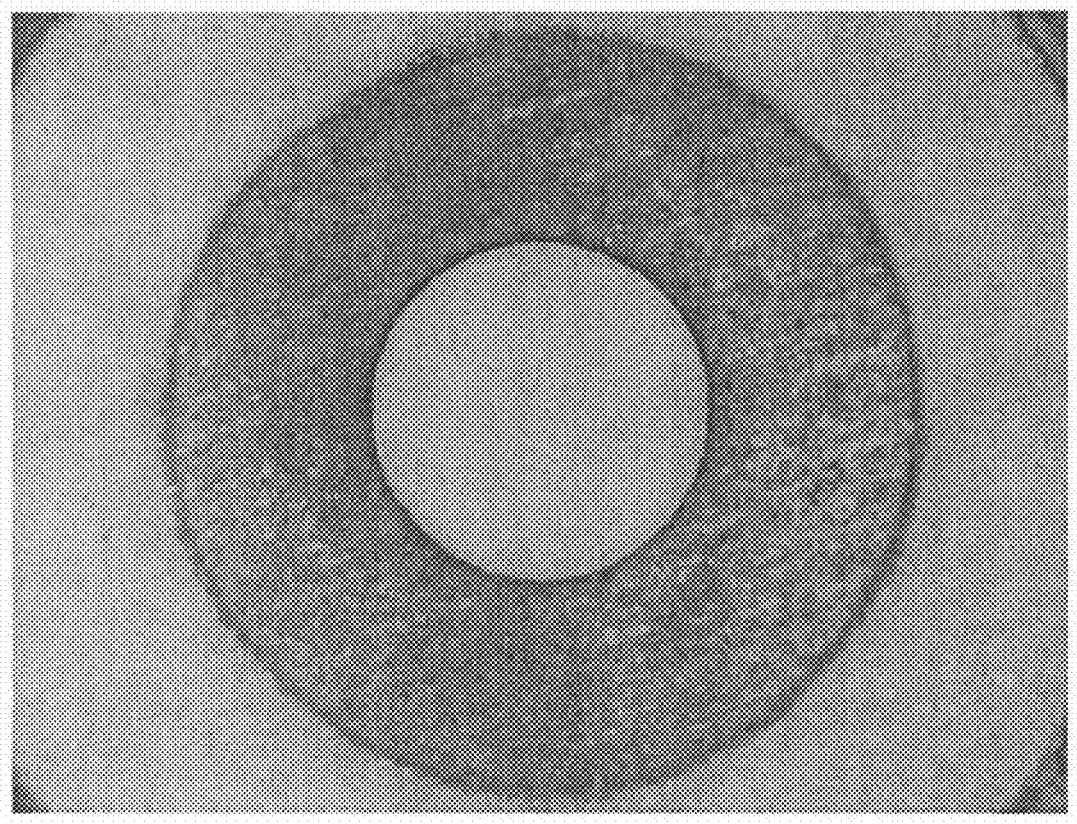
FIG. 3B shows a cross sectional cut through the chromatography column depicted in FIG. 3A, showing the exterior thermoplastic overcladding, shrinkable tube and interior porous monolith.

FIG. 3 shows a photograph of an actual chromatography column formed as described for FIG. 2 using a liquid crystal polymer coating. In FIG. 3B, a cross section is shown obtained by cutting the chromatography column of FIG. 3A across. The cross section demonstrates that the porous monolith is in liquid tight contact with the support, and no gaps between the porous monolith and the support are visible, thereby providing a chromatography column suitable for performing chromatographic separations.

Various aspects and embodiments will be illustrated in greater detail below.

II. Supports

The support can be any shape and size suitable for its intended use that is capable of providing support for and/or containing the porous inorganic substrate, and that softens at a suitable temperature. The support shape can be substantially flat or curved, tubular or cylindrical, square or rhombic, etc., without limitation. The support can be in the form of a wall to surround and contain the porous inorganic substrate, or can be in a bulk shape lacking recognizable wall structures, so long as the support provides a liquid tight contact with the porous inorganic substrate upon heating to a softening temperature.

The support "contains" the porous inorganic substrate in the sense of providing support and control over the substrate and allowing the porous inorganic substrate to be placed in contact or working relationship with associated apparatus. The substrate may be fragile and/or need to be kept in controlled environmental conditions, such as exposed, or not exposed, to the air or specific gases or liquids, and the support can contain the substrate so as to provide the desired mechanical, chemical, electrical, etc., environment of use for a particular application. The porous inorganic substrate is supported when the support provides a means for inserting the porous substrate into a housing or another device without damaging the surface or exposing the porous substrate to undesirable environmental conditions, or allows the porous substrate to become a part of an apparatus, for example.

In certain embodiments, the porous inorganic substrate is cylindrical and the support is tubular, containing the porous substrate along its axis but open or partially open at either end. However, the porous substrate could be contained at both ends, or only partially contained by the support, e.g., where the support covers a portion of the porous substrate but not the entire surface. In additional embodiments, the porous substrate can be substantially planar or two dimensional, and the support can contain the substrate on one side only, or both sides, or at the edges only, without limitation. Indeed, one skilled in the art can readily envision many possible arrangements and geometries of porous substrate and support for the applications described herein.

In a preferred embodiment, a support is provided in the form of a tube for containing a porous monolith. In one embodiment, the support can be formed from a sol gel monolith by any method known in the art. For example, the tubular support can be formed using the process described in U.S. Pat. No. 5,922,099 to Yoon, wherein a sol gel tube is formed and dried from the outside in to reduce the formation of cracks; using the sol gel extrusion process described in U.S. Pat. No. 6,080,339 to Fleming; for example.

In another preferred embodiment, the support is in the form of a tube formed from glass, for example a low melting borosilicate glass, and the porous inorganic substrate is a porous monolith, wherein upon assembly of the porous monolith inside the glass tube, the assembly is heated to the softening point of the glass tube, and the glass tube softens or melts to form an assembly having liquid tight contact between the porous monolith and the glass tube.

In another embodiment, an additional support can be included if desired. For example, a porous inorganic substrate can be assembled inside a glass tube, and the entire assembly can be placed inside a second larger glass tube. Additional outer protective layers can also be included (e.g., metal, or polymers) as needed for protection or assembly into a finished device or apparatus. Further processing steps are also possible (e.g., heating to anneal, temper or shrink) to further modify the additional layers to provide the desired configuration and contact with the supported substrate.

One skilled in the art will readily envision suitable supports and support compositions having the desired melting or softening temperatures, thicknesses, shapes, mechanical and/or electrical properties, resistance to acids/bases/solvents, and the like. Typical supports comprise silica based glasses, which may be pure (e.g., quartz) or doped with suitable dopants to provide the desired qualities. For example, fused silica, such as used in preparation of optical quality glass, fiber optics and the like, melts at a high temperature of approximately 1800-2000° C., softens at 1580° C., and is shrinkable at temperatures as low as approximately 1700° C. The presence of non-silica components lowers the thermal characteristics of the glasses. For example, borosilicate glasses soften at lower temperatures, of approximately 750-900° C., while soda glasses soften at approximately 700° C. Table 1 presents some representative glasses and the approximate temperatures at which they soften. The data presented are approximate for some glasses, and technical specifications are available from the manufacturer to ascertain the more exact softening temperatures, as the presence of varying amounts of additives alters the characteristics of the glass. For example, the softening temperature for DURAN® is 825° C. while the softening temperature for PYREX® is 821° C.

TABLE 1

Physical Properties of Representative Glasses

| | | Type of Glass | | | |
|---|---|---|---|---|---|
| | Soda Lime | Borosilicate (D 263 T, Schott; DURAN®, PYREX®, Corning) | AF 45 (Schott) alkali free borosilicate | VYCOR® 7913 (Corning) | Quartz (fused silica) |
| Softening range | 696° C. | 736-825° C. | 883° C. | 1530° C. | 1580° C. |

Some additional glasses are representative of the scope of the present invention, but the present invention is not limited to any particular glass. For example, AF 45 (Schott North America, Inc., Elmsford, N.Y.) is an alkali free borosilicate with a high proportion of BaO and $Al_2O_3$. D 263 T is a borosilicate glass manufactured using high purity raw materials. VYCOR® is the tradename for a 96% silica glass suited for high temperature applications (LIp to 900° C.) sold by Corning Specialty Materials, Corning, N.Y. The softening temperature for a glass is generally about 200° C. greater than its $T_g$ (glass transformation temperature).

Low temperature melting glasses include those described in, for example, U.S. Pat. No. 4,323,654 to Tick, which describes alkali-$Ta_2O_5$—$B_2O_3$—$P_2O_5$ glasses for molded optics having high refractive index and a glass transition temperature below 500° C. Another example is U.S. Pat. No. 3,926,649 to Ray, which describes alkali borophosphate glasses comprising $P_2O_5$:$B_2O_3$ in a ratio from 15:1 to 6:1, only a small proportion of minor constituents such as $SiO_2$ and $Al_2O_3$, and preferably containing at least one alkali metal oxide such as $Li_2O$, $Na_2O$ and $K_2O$ together with at least one alkaline earth or zinc oxide, such as MgO, CaO and BaO. The glasses were reported to exhibit glass transition temperatures below 225° C. and varying water solubilities at 100° C.

One skilled in the art can readily determine a glass having desired characteristics such as low or high water solubility, melting or softening temperatures, and the like. For some applications, glasses with high solubility in water might be acceptable because only nonaqueous solvents are in use, or no solvents at all are in use (e.g., for gaseous applications), or eventual dissolution of the glass support is a desired feature.

III. Porous Inorganic Substrates

Porous inorganic substrates can include any porous ceramics, glasses, metals, and the like, providing that the porous inorganic substrate is stable under the conditions utilized for enclosing the porous inorganic substrate within the shrinkable support. The porous inorganic substrate is stable to conditions utilized by being chemically and mechanically resistant to the temperatures and pressures involved in the process, i.e., not being readily deformable, vaporizable, or melting.

It is preferred that the porous inorganic substrates are monolithic rather than particulate in composition. Preferably, the porous inorganic substrate has a total porosity of at least 5%. In certain embodiments, the porous substrate is characterized by a total porosity of at least 60% and in certain additional embodiments, the porous substrate is characterized by a total porosity of from about 85% to about 97%. In particularly preferred embodiments, the porous inorganic substrate is a porous monolith comprising an inorganic material and having a total porosity of at least 5%. In certain embodiments, the porous monolith is characterized by a mesopore mode distribution of about 2 nm to about 50 nm, and in other embodiments, the porous monolith is characterized by a mesopore mode distribution of about 20 nm to about 50 nm, and a mesopore volume of at least 0.2 cc/g, and more preferably, at least 1.0 cc/g. However, the porosity and specific pore characteristics of the porous inorganic substrate are not limited, and can be chosen to suit particular applications.

Monolithic materials can include monolithic forms of any material suitable for use with high temperatures, and can be made from ceramics and glasses, or metals, or the like. Further, the porous monoliths can be prepared by any method known in the art. For example, in certain embodiments, the porous monolith can comprise a metal, such as silver, copper, titanium, or cobalt, etc., and can be prepared as described in U.S. Pat. No. 7,141,675 to Tappan for the production of nanoporous metal foam. In preferred embodiments, the porous monolithic material is a glass or ceramic prepared using a sol gel method.

A. Sol Gel Monoliths

Sol gel precursors include metal and metalloid compounds having hydrolyzable ligands that can undergo a sol gel reaction and form sol gels. Suitable hydrolyzable ligands include hydroxyl, alkoxy, halo, amino, or acylamino, without limitation. The most common metal oxide participating in the sol gel reaction is silica, though other metals and metalloids are also useful, such as zirconia, vanadia, titania, niobium oxide, tantalum oxide, tungsten oxide, tin oxide, hafnium oxide and alumina, or mixtures or composites thereof, having reactive metal oxides, halides, amines, etc., capable of reacting to form a sol gel. Additional metal atoms that can be incorporated into the sol gel precursors include magnesium, molybdenum, cobalt, nickel, gallium, beryllium, yttrium, lanthanum, tin, lead, and boron, without limitation.

Preferred metal oxides and alkoxides include, but are not limited to, silicon alkoxides, Such as tetramethylorthosilane (TMOS), tetraethylorthosilane (TEOS), fluoroalkoxysilane, or chloroalkoxysilane, germanium alkoxides (such as tetraethylorthogermanium (TEOG)), vanadium alkoxides, aluminum alkoxides, zirconium alkoxides, and titanium alkoxides. Similarly, metal halides, amines, and acyloxy derivatives can also be used in the sol gel reaction.

In preferred embodiments, the sol gel precursor is an alkoxide of silicon, germanium, aluminum, titanium, zirconium, vanadium, or hafnium, or mixtures thereof. In particularly preferred embodiments, the sol gel precursor is a silane. In a more preferred embodiment, the sol gel precursor is a silane such as TEOS or TMOS.

In particular embodiments, the sol gel precursor can further include an organic substituent. Accordingly, a sol gel monolith formed from sol gel precursors including organic substituents comprises an inorganic-organic hybrid monolithic material. Sol gel precursors comprising an organic substituent include, without limitation, organosilanes having saturated or unsaturated hydrocarbyl substituents, such as an alkyltrialkoxysilane, cycloalkyltrialkoxysilane, dialkyldialkoxysilane, trialkylalkoxysilane, tetraalkoxysilane, vinyltrialkoxysilane, allyltrialkoxysilane, aryl substituents, such as phenylalkyldialkoxysilane, diphenylalkoxysilane, or naphthyltrialkoxysilane, or mixtures thereof. The sol gel precursor comprising an organic substituent can also include other organometallic compounds such as organogermanes, or organosubstituted titanium, aluminum, zirconium or vanadium alkoxides, and the like. Suitable hydrocarbyl substituents can be $C_{1-100}$ or more typically $C_{1-30}$. In another preferred embodiment, the silane is a mixture of silanes comprising a trialkoxysilane and a tetraalkoxysilane. In addition, the sol gel monolith can be surface modified with an organic substituent, such as a bonded phase comprising an alkylsilane or an endcapping reagent, or the like. In these embodiments, the sol gel monolith must be treated at temperatures that do not destroy the desired organic functionalities, or the organic substituents must be added after heating at temperatures that would destroy the organic substituents.

In additional embodiments, a porous monolith can be prepared from particles that are modified and coalesced or sintered to form a monolithic material. For example, U.S. Patent Application Publication No. 2003/0150811 to Walter describes a process for forming a porous inorganic/organic hybrid material reportedly involving first forming porous inorganic/organic hybrid particles, modifying the pore structure of the porous hybrid particles, and coalescing the porous hybrid particles to form a monolith material, and optionally further treating the monolith with a hydrothermal treatment in order to modify the pore structure. In such embodiments, the porous monolith can be either inorganic or an inorganic-organic hybrid material depending on the composition of the particles used.

In certain embodiments, porous monolithic materials can be prepared using sol gel methods such as those described in U.S. Pat. Nos. 5,009,688, 5,624,875 and 6,207,098 to Nakanishi, U.S. Pat. No. 5,100,841 to Wada, U.S. Pat. No. 6,398,962 to Cabrera, and the like. For example, U.S. Pat. No. 5,009,688 to Nakanishi reports that dissolved organic polymer undergoes phase separation during the hydrolysis and polymerization of the metal alkoxide or its oligomer and a porous product is produced. The porous gel is heated to calcine and convert the gel to a $SiO_2$ type porous ceramic having improved mechanical strength. Particular structures formed from sol gels that form hierarchically ordered porous oxides, such as those described in U.S. Pat. No. 6,541,539 to Yang, et al., or mesoscopically ordered materials such as those described in U.S. Pat. No. 6,592,764 to Stucky, et al., can also be utilized advantageously as described herein.

Alternative methods to form a porous monolith include those described in U.S. Pat. Nos. 6,884,822, 7,026,362 and 7,125,912 to Wang. These patents describe that use of HF can promote the formation of larger pore sizes, thus reducing the tendency for cracking of gel monoliths. However, the inventors point out that the use of catalysts such as HF also shortens gelation times, and can result in insufficient time for processing, or for bubbles to diffuse out of the gel, thereby degrading the quality of the gel produced. A method of manufacturing a xerogel monolith is described that includes preparing a first solution comprising metal alkoxide, a second solution comprising a catalyst, and mixing the first and second solutions together, where at least one of the solutions is cooled to achieve a mixture temperature for the third solution which is substantially below room temperature. In so doing, the mixture reportedly has a significantly longer gelation time at the mixture temperature as compared to a room temperature.

In a preferred embodiment, the sol gel monolith is prepared using the method described in co-pending U.S. Patent Publication No. 2006/0131238, which produces a porous monolith of high porosity characterized by the presence of mesopores and macropores and lacking micropores.

B. Porogens

Porogens can be utilized as an aid in the preparation of a porous monolith when using the sol gel process. For example, U.S. Pat. No. 5,009,688 to Nakanishi reports the used of dissolved organic polymers, such as polystyrene sulfonic acid, polyacrylic acid, polyallylamine, polyethylene-imine, polyethylene oxide, or polyvinyl pyrrolidone, to introduce pores during hydrolysis and polymerization of the sol gel precursors. Preparation of the sol gel monolith in the presence of the phase separated volumes provides a sol gel monolith possessing macropores and/or large mesopores, which provide greater porosity to the sol gel monolith, and provide superior flow rates for solvent.

In one embodiment, the porogen can be a hydrophilic polymer. The amount and hydrophilicity of the hydrophilic polymer in the sol gel forming solution affects the pore volume and size of macropores formed, and generally, no particular molecular weight range is required, although a molecular weight between about 1,000 to about 1,000,000 g/mole is preferred. The porogen can be selected from, for example, polyethylene glycol (PEG), sodium polystyrene sulfonate, polyacrylate, polyallylamine, polyethyleneimine, polyethylene oxide, polyvinylpyrrolidone, poly(acrylic acid), and can also include polymers of amino acids, and polysaccharides such as cellulose ethers or esters, such as cellulose acetate, or the like. Preferably, the polymer is a PEG having a molecular weight up to about 1,000,000 g/mole.

The porogen can also be an amide solvent, such as formamide, or an amide polymer, such as poly(acrylamide), or a surfactant, such as a nonionic surfactant, an ionic surfactant, an amphiphilic surfactant, or mixtures thereof. A preferred surfactant is the nonionic surfactant Pluronic F68 (also known as Poloxamer).

Exemplary surfactants are those having an HLB value of between about 10-25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like.

Nonionic surfactants are preferred in certain embodiments and include, for example, polyoxyl stearates such as polyoxyl 40 stearate, polyoxyl 50 stearate, polyoxyl 100 stearate, polyoxyl 12 distearate, polyoxyl 32 distearate, and polyoxyl 150 distearate, and other Myrj™ series of surfactants, or mixtures thereof. Yet another class of surfactant useful as porogens are the triblock co-polymers of ethylene oxide/propylene oxide/ ethylene oxide, also known as poloxamers, having the general formula $HO(C_2H_4O)_a(-C_3H_6O)_b(C_2H_4O)_aH$, available under the tradenames Pluronic and Poloxamer. Other useful surfactants include sugar ester surfactants, sorbitan fatty acid esters such as sorbitan monolaurate, sorbitan monopalmitate, sorbitan monostearate, sorbitan tristearate, and other Span™ series surfactants, glycerol fatty acid esters such as glycerol monostearate, polyoxyethylene derivatives such as polyoxyethylene ethers of high molecular weight aliphatic alcohols (e.g., Brij 30, 35, 58, 78 and 99) polyoxyethylene stearate (self emulsifying), polyoxyethylene 40 sorbitol lanolin derivative, polyoxyethylene 75 sorbitol lanolin derivative, polyoxyethylene 6 sorbitol beeswax derivative, polyoxyethylene 20 sorbitol beeswax derivative, polyoxyethylene 20 sorbitol lanolin derivative, polyoxyethylene 50 sorbitol lanolin derivative, polyoxyethylene 23 lauryl ether, polyoxyethylene 2 cetyl ether with butylated hydroxyanisole, polyoxyethylene 10 cetyl ether, polyoxyethylene 20 cetyl ether, polyoxyethylene 2 stearyl ether, polyoxyethylene 10 stearyl ether, polyoxyethylene 20 stearyl ether, polyoxyethylene 21 stearyl ether, polyoxyethylene 20 oleyl ether, polyoxyethylene 40 stearate, polyoxyethylene 50 stearate, polyoxyethylene 100 stearate, polyoxyethylene derivatives of fatty acid esters of sorbitan such as polyoxyethylene 4 sorbitan monostearate, polyoxyethylene 20 sorbitan tristearate, and other Tween™ series of surfactants, phospholipids and phospholipid fatty acid derivatives such as lecithins, fatty amine oxides, fatty acid alkanolamides, propylene glycol inonoesters and monoglycerides, such as hydrogenated palm oil monoglyceride, hydrogenated soybean oil monoglyceride, hydrogenated palm stearine monoglyceride, hydrogenated vegetable monoglyceride, hydrogenated cottonseed oil monoglyceride, refined palm oil monoglyceride, partially hydrogenated soybean oil monoglyceride, cotton seed oil monoglyceride sunflower oil monoglyceride, sunflower oil monoglyceride, canola oil monoglyceride, succinylated monoglycerides, acetylated monoglyceride, acetylated hydrogenated vegetable oil monoglyceride, acetylated hydrogenated coconut oil monoglyceride, acetylated hydrogenated soybean oil monoglyceride, glycerol monostearate, monoglycerides with hydrogenated soybean oil, monoglycerides with hydrogenated palm oil, succinylated monoglycerides and monoglycerides, monoglycerides and rapeseed oil, monoglycerides and cottonseed oils, monoglycerides with propylene glycol monoester sodium stearoyl lactylate silicon dioxide, diglycerides, triglycerides, polyoxyethylene steroidal esters, Triton-X series of surfactants produced from octylphenol polymerized with ethylene oxide, where the number "100" in the trade name is indirectly related to the number of ethylene oxide units in the structure, (e.g., Triton X-100™ has an average of N=9.5 ethylene oxide units per molecule, with an average molecular weight of 625) and having lower and higher mole adducts present in lesser amounts in commercial products, as well as compounds having a similar structure to Triton X-100™, including Igepal CA-630™ and Nonidet P-40M (NP-40™, N-lauroylsarcosine, Sigma Chemical Co., St. Louis, Mo.), and the like. Any hydrocarbon chains in the surfactant molecules can be saturated or unsaturated, hydrogenated or unhydrogenated.

An especially preferred family of surfactants are the poloxamer surfactants, which are a:b:a triblock co-polymers of ethylene oxide:propylene oxide:ethylene oxide. The "a" and "b" represent the average number of monomer units for each block of the polymer chain. These surfactants are commercially available from BASF Corporation of Mount Olive, N.J., in a variety of different molecular weights and with different values of "a" and "b" blocks. For example, Lutrol® F127 has a molecular weight range of 9,840 to 14,600 and where "a" is approximately 101 and "b" is approximately 56, Lutrol F87 represents a molecular weight of 6,840 to 8,830 where "a" is 64 and "b" is 37, Lutrol F108 represents an average molecular weight of 12,700 to 17,400 where "a" is 141 and "b" is 44, and Lutrol F68 represents an average molecular weight of 7,680 to 9,510 where "a" has a value of about 80 and "b" has a value of about 27.

Sugar ester surfactants include sugar fatty acid monoesters, sugar fatty acid diesters, triesters, tetraesters, or mixtures thereof, although mono- and di-esters are most preferred. Preferably, the sugar fatty acid monoester comprises a fatty acid having from 6 to 24 carbon atoms, which may be linear or branched, or saturated or unsaturated $C_6$ to $C_{24}$ fatty acids. The $C_6$ to $C_{24}$ fatty acids are preferably chosen from stearates, behenates, cocoates, arachidonates, palmitates, myristates, laurates, carprates, oleates, laurates and their mixtures, and can include even or odd numbers of carbons in any subrange or combination. Preferably, the sugar fatty acid monoester comprises at least one saccharide unit, such as sucrose, maltose, glucose, fructose, mannose, galactose, arabinose, xylose, lactose, sorbitol, trehalose or methylglucose. Disaccharide esters such as sucrose esters are most preferable, and include sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose polyesters, such as sucrose pentaoleate, hexaoleate, heptaoleate or octooleate, and mixed esters, such as sucrose palmitate/stearate.

Particularly preferred examples of these sugar ester surfactants include those sold by the company Croda Inc of Parsippany, N.J. under the names Crodesta F10, F50, F160, and F110 denoting various mono-, di- and mono/di ester mixtures comprising sucrose stearates, manufactured using a method that controls the degree of esterification, such as described in U.S. Pat. No. 3,480,616.

Use may also be made of those sold by the company Mitsubishi under the name Ryoto Sugar esters, for example under the reference B370 corresponding to sucrose behenate formed of 20% monoester and 80% di-, tri- and polyester. Use may also be made of the sucrose mono- and dipalmitate/stearate sold by the company Goldschmidt under the name "Tegosoft PSE". Use may also be made of a mixture of these various products. The sugar ester can also be present in admixture with another compound not derived from sugar; and a preferred example includes the mixture of sorbitan stearate and of sucrose cocoate sold under the name "Arlatone 2121" by the company ICI. Other sugar esters include, for example, glucose trioleate, galactose di-, tri-, tetra- or pentaoleate, arabinose di-, tri- or tetralinoleate or xylose di-, tri- or tetralinoleate, or mixtures thereof. Other sugar esters of fatty acids include esters of methylglucose include the distearate of inethylglucose and of polyglycerol-3 sold by the company Goldschmidt under the name of Tegocare 450. Glucose or maltose monoesters can also be included, such as methyl O-hexadecanoyl-6-D-glucoside and O-hexadecanoyl-6-D-maltose. Certain other sugar ester surfactants include oxyethylenated esters of fatty acid and of sugar include oxyethylenated derivatives such as PEG-20 methylglucose sesquistearate, sold under the name "Glucamate SSE20", by the company Amerchol.

One of the characteristics of surfactants is the HLB value, or hydrophilic lipophilic balance value. This value represents the relative hydroplicility and relative hydrophobicity of a surfactant molecule. Generally, the higher the HLB value, the greater the hydrophilicity of the surfactant while the lower the HLB value, the greater the hydrophobicity. For the Lutrol® molecules, for example, the ethylene oxide fraction represents the hydrophilic moiety and the propylene oxide fraction represents the hydrophobic fraction. The HLB values of Lutrol F127, F87, F108, and F68 are respectively 22.0, 24.0, 27.0, and 29.0. The preferred sugar ester sulfactants provide HLB values in the range of about 3 to about 15.

IV. Characterization of the Pore Structure of a Porous Inorganic Substrate

The pore size distribution curve can be determined from the derivative of the pore volume (V) with respect to the pore diameter (D) (dV/d log D), plotted against the pore diameter (D). The mode pore size is the pore size for which the value of dV/d log D of the pore size distribution curve is greatest (the maximum peak exhibited). This pore size distribution curve is derived from the adsorption isotherm obtained by measurement of the adsorption of nitrogen gas, for example, according to several equations. The adsorption isotherm measurement method generally involves cooling the sample to liquid nitrogen temperature, introducing nitrogen gas, and determining the amount of nitrogen adsorbed by fixed displacement or gravimetry. The pressure of the introduced nitrogen gas is gradually increased, and the adsorption of nitrogen gas at each equilibrium pressure is plotted to produce an adsorption isotherm. The pore size distribution curve can be derived from this adsorption isotherm according to the equation for the Cranston-Inklay method, Dollimore-Heal method, BET method, BJH method, and so forth.

As described herein, the total surface area and micropore volume can be conveniently determined using an instrument such as the Micromeritics TriStar 3000. The total surface area is preferably calculated using the BET method, and the micropore volume is calculated using the t-plot method, as described in by Mikail, R., et al. (1968) *J. Colloid Interface Sci.* 26, 45. The t-plot method can be used to detect the presence of the micropores in the sample, and to determine their volume. The t-plot is a curve of the nitrogen adsorption (v/g) plotted against the mean film thickness (t) of the adsorption film (where the x-axis is the mean film thickness and the y-axis is the adsorption). The amount of nitrogen adsorbed versus thickness of the layer is linear if no micropores or inesopores exist. Conversely, the presence of micropores can be detected by the loss of nitrogen adsorption at a particular thickness, and the diameter of the pore that no longer provides accessible surface areas can be calculated.

V. Methods for Preparing a Supported Porous Inorganic Substrate

In additional embodiments, methods are provided for forming a supported porous substrate comprising: a) assembling a porous inorganic substrate into a shrinkable support comprising an inorganic material to provide an assembly, and b) shrinking the support onto the porous substrate by heating the assembly to a temperature that is effective to shrink the support onto the porous substrate such that there is liquid tight contact between the porous inorganic substrate and the support.

Preferably, the porous substrate is a porous monolith comprising an inorganic material such as glass, ceramic or metal. In certain preferred embodiments, the porous monolith is a porous glass monolith made using a sol-gel method. In alternative embodiments, the porous monolith is formed from particles that are modified to form a monolith.

In particular embodiments, the porous substrate or the porous monolith is formed separately from said shrinkable support and inserted therein prior to shrinking. In additional embodiments, the porous inorganic substrate or porous monolith is formed inside said shrinkable support prior to shrinking. The porous inorganic substrate may be introduced by packing, coating, impregnating, cladding, wrapping, or other art-recognized techniques, etc., depending on the requirements of the particular device.

Preferably, the shrinkable support is formed from an inorganic material such as a glass or ceramic. In particular embodiments, the shrinkable support is made by a sol-gel process.

In particular embodiments, the temperature that is effective to shrink the support onto the porous inorganic substrate is a temperature that is effective to soften the support (e.g., the softening temperature) allowing the support to shrink to form a liquid tight contact with the porous inorganic substrate. Preferably, the temperature effective to shrink the support onto the porous monolith has no affect or only limited affect on the pore distribution of the porous monolith. In particular embodiments, the temperature that is effective to shrink the support onto the porous monolith is less than about 2000° C., and more preferably is less than about 1000° C.

In certain embodiments, the porous inorganic substrate and support are initially separated by a gap, such as occurs, for example, when the porous substrate is formed separately and inserted into tubular support, and upon heating to a temperature effective to soften the support, the support shrinks onto the porous inorganic substrate so that the gap is minimized and the porous substrate and the support are in liquid tight contact. Additionally, the porous substrate can be formed in the support, and when dried and/or calcined, separates from contact with the Support substrate. Heating can then be performed to shrink the support onto the porous substrate so that the gap is minimized and there is liquid tight contact between them. Alternatively, the porous substrate is formed in the support without a gap being present between them, and subsequent heating shrinks the support either simultaneously with the shrinking of the porous substrate as it is calcined, or after the porous substrate is calcined, such that there is no gap between them at least upon completion of the heat treatment. In some embodiments, there is no gap between them at any stage in the process. In preferred embodiments, the substrate is a porous monolith, and more preferably, is a porous glass monolith. In other embodiments, a vacuum is applied to the support that is sufficient to lower the temperature at which shrinkage occurs.

In a particular embodiment, a vacuum is applied to the interior of the support, for example to one end of a tube (e.g., an unheated end), wherein the application of vacuum results in a decrease in the temperature at which shrinkage occurs. By appropriate choice of porous inorganic substrate (choice of monolithic or nonmonolithic substrate, optionally having a desired composition, porosity and/or pore characteristics), and support (having a particular softening temperature), and performing the shrinkage step in the appropriate conditions (e.g., with or without a vacuum applied to the support), an article or device can be obtained having desired porosity and/or pore characteristics and a liquid tight contact between the porous substrate and the support.

The lower range of temperatures that are effective to shrink the support into liquid tight contact with the porous substrate is not particularly limited, and can be chosen based on the characteristics of the porous substrate desired and controlled by the amount of vacuum applied, and the softening temperature of the support. The effective temperature is at least 100° C., and more preferably, the temperature is between about 200° C. and 2000° C. In particular embodiments, the effective temperature is between about 100° C. and 400° C. In other embodiments, the effective temperature is between about 200° C. and 900° C. In yet other embodiments, the effective temperature is between about 400° C. and 1000° C. In other embodiments, the effective temperature is between about 300° C. and 700° C.

For example, a low softening temperature glass could be used with a porous monolith having a structure having a desired micropore size distribution and surface area, and the shrinkage step could be performed at a relatively low temperature (e.g., 200° C.) such that the micropore structure is preserved. A higher softening temperature glass could be used with a porous substrate having a desired mesopore distribution because the mesopore distribution is less likely to be affected by high temperature than the micropore distribution. If the pore characteristics of the porous substrate are not particularly limiting, then the softening temperature of the support is not particularly limiting, and a higher or lower softening temperature can be utilized, as desired for a particular application.

In the Examples below, the temperature utilized for shrinking was 850° C., which is an acceptable shrinkage temperature for the borosilicate glass support used and the sol gel monolith of high porosity prepared. However, for these embodiments, an effective temperature range could be from about 400° C. to about 1000° C.

VI. Applications and Methods of Use

The articles and devices described herein have a wide variety of end uses in the separation and catalytic sciences, such as materials for chromatographic columns, filtration membranes, e.g., for reverse osmosis, ultrafiltration, preparative filtration and the like, microtiter plates, scavenger resins, solid phase organic synthesis supports, fuel cells, sensor arrays, optoelectronic devices, hydrogen storage devices, and the like. In a preferred embodiment, the application is in the field of chromatography and the articles and devices provide liquid tight contact between the support and the porous inorganic substrate, which serves as the stationary phase, and the chromatographic device exhibits improved elution profiles due to reduced peak broadening and increased chromatographic efficiency. In another embodiment, the application is in the field of catalysis, and the porous substrate can further comprise catalytic functionalities such as enzymes or metals, and the like. In a particularly advantageous embodiment, the article is a chromatographic device, e.g., a chromatographic column, such as commonly used in HPLC.

Ordinarily, applications such as TLC and microfluidics do not require a shrinkable support as there is insufficient shrinkage of the porous monolith as it forms in contact with the support to cause separation and undesired leakage. However, for instances where there is substantial shrinkage of the porous monolith, or when leakage of fluid between the porous monolith and the support would result in unacceptable performance, use of a shrinkable support can restore the liquid tight contact that is needed for optimal functioning. For example, if a sol gel formed inside a microfluidic channel separates from contact with the microfluidics support substrate, use of a shrinkable support can restore the liquid tight contact that is needed for optimal functioning of the microfluidics device.

Accordingly, in one embodiment, there is provided a chromatography column for performing liquid chromatography (including HPLC) comprising a porous monolith contained within a glass support, and further adapted for liquid chromatography by the addition of the necessary end fittings, tubing and the like.

In an additional embodiment, there is provided a capillary chromatography column comprising a stationary phase comprising a porous monolith contained within a capillary, wherein the capillary and porous monolith are together subjected to shrinkage, e.g., calcination.

In an additional aspect, there is provided a method for separating a mixture of analytes in a sample, said method comprising the steps of a) providing a chromatographic device, particularly a chromatographic column, comprising a porous inorganic substrate enclosed inside a glass tubing, wherein the column has been heated to shrink the glass tubing such that there is liquid tight contact between the porous inorganic substrate and the glass tubing; b) applying the sample to the chromatographic column; c) eluting the chromatographic column with a mobile phase; and d) collecting the separated analytes eluting from the chromatographic column. Preferably, the porous substrate is a porous monolith. Suitable separations can be performed using thin layer chromatography, high performance liquid chromatography, reversed phase chromatography, normal phase chromatography, ion chromatography, ion pair chromatography, reverse phase ion pair chromatography, ion exchange chromatography, affinity chromatography, hydrophobic interaction chromatography, size exclusion chromatography, chiral recognition chromatography, perfusion chromatography, electrochromatography, partition chromatography, microcolumn liquid chromatography, capillary chromatography, capillary zone electrophoresis (CZE), nano-LC, open tubular liquid chromatography (OTLC), capillary electrochromatography (CEC), liquid-solid chromatography, preparative chromatography, hydrophilic interaction chromatography, supercritical fluid chromatography, precipitation liquid chromatography, bonded phase chromatography, fast liquid chromatography, flash chromatography, liquid chromatography-mass spectrometry, gas chromatography, microfluidics based separations, chip based separations or solid phase extraction separations.

The articles and methods of the present invention can be advantageously used in chromatographic and analytical separations applications in the form of chromatographic columns or other devices, where such devices have improved flow properties, reduced back pressure, controlled pore size distributions, and potentially reduced silanol residues, which eliminate peak tailing for basic analytes. For example, the porous monolith can be incorporated into capillary column, cartridge system, or conventional HPLC system, or the like. Since the substrates described herein are substantially rigid, e.g., monolithic sorbents, and dead space may arise during the cladding, the cladding of the substrates or monoliths to provide columns, filters, or cartridges or the like having no dead space and in a pressure-stable manner can be challenging. In one embodiment, the substrate or sol gel monolith can be used to prepare a cartridge, for example, as described in U.S. Pat. No. 6,797,174, which describes a clad column with a monolithic sorbent on which a cap is installed at least at one end, and a connecting system consisting of at least one divided supporting screw and at least one end piece which is screwed onto the supporting screw for the connection of eluent feed and discharge. Alternatively, the substrate or porous monolith can be incorporated into a cartridge system without the use of a cap. Use of a shrinkable support as described herein, and heating to shrink the support onto the porous substrate, provides for improved systems.

In a particularly advantageous embodiment, the chromatographic device is a chromatographic column, such as an HPLC column. FIG. 3B shows a micrograph of a cross-section of a porous sol gel monolith in glass tubing. The tubing had an initial internal diameter of 1.8 mm, and was shrunk onto the calcinated porous monolith having a diameter of 1.2 mm. The porous monolithic structure can be seen, and the liquid tight contact with no gaps between the monolith and the tubing. Such a chromatographic device can be advantageously applied to HPLC separations with improved chromatographic performance.

The supported porous monoliths can also be used with a planar support for planar applications (e.g., TLC, or the like), or as a component of devices such as microfluidics devices, as well as other potentially planar geometries such as filtration devices and membranes, solid phase extraction media, microtiter plates, fuel cells, optoelectronics devices. Any shape can be formed, without limitation, such as rod shaped, spheres, hollow or filled structures (e.g., hollow tubes), flat sheets, fibers, chips, micro- or nano- sized wires or other shapes useful in chromatography, adsorption, catalysis, or other applications. The supported porous substrates can also be treated so as to modify its pore structure or surface chemistry. For example, polymeric, organic or inorganic phases and/or layers can be bonded and/or coated onto porous substrate surfaces to provide particular adsorption or catalytic properties.

The supported porous substrates can also be used in other applications, such as filtration, solid phase synthesis, bioreactors, catalysis, resins, sensor devices, medical devices and drug or other active agent delivery platforms, fuel cells, optoelectronics devices, and the like. The methods are also applicable to the preparation of devices for carrying out such applications. The supported porous substrates can include inorganic as well as organic or biological components. The supported porous monoliths can be used as a stationary phase that includes ultraporous inorganic/organic and/or biological hybrid materials. The stationary phase may be introduced by polymerization in situ or by inserting and shrinking the support onto the porous monolith as described herein, depending on the requirements of the particular device. In a preferred embodiment, the porous monolith is formed in situ in such devices. In another preferred embodiment, the porous sol gel monolith is formed in a mold and transferred to the support for shrinkage of the support onto the porous monolith, optionally at the site of intended use.

In particular embodiments, the porous sol gel monoliths of the invention can be used in a method of preparing devices for capillary and microfluidics applications, which typically utilize small column internal diameters (<100 micron i.d.) and low mobile phase flow rates (<300 mL/min). Techniques such as capillary chromatography, capillary zone electrophoresis (CZE), nano-LC, open tubular liquid chromatography (OTLC), and capillary electrochromatography (CEC) offer numerous advantages over conventional scale high performance liquid chromatography (HPLC). These advantages include higher separation efficiencies, high-speed separations, analysis of low volume samples, and the coupling of 2-dimensional techniques. However, even these applications can benefit from the ultraporous sol gel monoliths described herein, which provides the possibility of even higher flow rates and more uniform and controllable pore size distributions.

Microchip-based separation devices have been developed for rapid sample analysis. Examples of microchip-based separation devices include those for capillary electrophoresis, capillary electrochromatography and high-performance liquid chromatography. For example, the sol gel monolith can be incorporated into a chromatographic chip, which can be made, for example, by forming grooves on a plate and forming a silica gel having a monolithic bimodal pore structure in the grooves. A representative chromatographic chip and method for preparing and using it is described in U.S. Patent Application Publication No. 2003/0230524 to Naohiro. These and other separation devices are capable of fast analyses and provide improved precision and reliability compared to other conventional analytical instruments. Compared to other conventional separation devices, these microchip-based separation devices have higher sample throughput, reduced sample and reagent consumption, and reduced chemical waste. The liquid flow rates for microchip-based separation devices range from approximately 1-300 nanoliters per minute for most applications. The ultraporous sol gel monoliths described herein can be incorporated into these microfluidics designs, providing a monolithic sorbent within microchannels on microchip-based separation device, thereby providing greater flow rates for microchip applications as well.

VII. Advantages of the Invention

Some advantages and characteristics the present articles and methods include:

Glass or ceramic tubes processed by shrinking as described herein have smoother inner surfaces than equivalent metal or plastic tubes. The smoother inner surfaces produce superior results in applications such as chromatography, where the smoother surface produces reduced edge effects and greater uniformity of flow of mobile phase through the substrate bed (rather than between the substrate bed and the containing walls). As a result, chromatography columns produced by the methods described herein provide greater chromatographic efficiency, improved peak shapes, and reduced diffusion broadening.

In addition, the inventive devices and methods provide liquid tight contact between the porous inorganic substrate and the support. When utilized in the preparation of chromatographic columns, the method provides increased chromatographic efficiency and improved separation, peak shape, peak height, and the like. In addition, the devices and methods provide superior flow rates and decreased separation times. Similarly, the devices and methods can provide superior catalytic efficiencies by virtue of the superior flow properties of the devices.

High processing and operating temperatures can be tolerated and excellent solvent resistance can be provided.

Good support is provided for high-porosity monolithic media which can be fragile, such as the ultraporous sol-gel monolith described in co-pending US Patent Publication No. 2006/0131238.

The support is sufficient to allow for fabrication of outer plastic structures.

Shrinkage of the support to achieve target dimensions and to compensate for any shrinkage in the porous substrate is readily controlled. The method can be readily scaled to work for parts of widely-varying dimensions.

There is no longer a need to perform surface modifications to the internal surfaces of glass supports or to perform additional gelation steps in an attempt to cause the porous monolith to adhere to the glass support. As a result, the entire manufacturing process is simple, cost-effective and reproducible.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric. All solvents were purchased as HPLC grade, and all reactions were routinely conducted in the air unless otherwise indicated.

EXAMPLE 1

Preparation of a Porous Monolith and a Support in Liquid Tight Contact

The nonionic surfactant Pluronic F68 (0.44 g, BASF) was dissolved in a mixture of 1.1 g water, 3.6 g methanol, 2.1 g reagent alcohol and 0.96 g HF (2.6 M). While stirring, 5.0 ml tetraethoxysilane (TEOS) was introduced into the above solution and formed a uniform mixture. After 5 minutes, the sol was injected into a polymer tubing of 1.6 mm inner diameter (ID). Thirty minutes later, the sol became white gels, which were then aged, dried and transferred to a furnace for calcination at a temperature of about 550° C. overnight. Gels were removed from the tubing prior to calcination.

The final outside-diameter of the porous monolith was about 1.2 mm. BET surface area, mesopore volume and mode diameter measurements were performed using a Micromeritics TriStar 3000: the BET surface area was about 400 $m^2/g$, the mesopore volume was 1.1 $cm^3/g$, and the mesopore diameter was about 100 Å. The total pore volume was estimated as about 5.0 $cm^3/g$ using mercury intrusion measurement.

The thus-formed silica monolith was then inserted into a 1.8 mm ID borosilicate glass tubing (Corning. Inc. Corning, N.Y.) which was subjected to heat treatment at a temperature of 850° C. in a furnace until the gel cylindrical surfaces were sealed by the glass.

After the gel cylindrical surfaces were completely sealed, the glass tubing and porous monolith was cut into 100 mm long pieces which were suitable for use as chromatography columns. The pieces were over-molded with the liquid crystal polymer (LCP), with both ends threaded for fittings. Extra glass was then cut off and polished to a desired column length of 50 mm.

The resulting chromatography column is shown in FIG. 3A. The cross section of the column (shown in FIG. 3B) demonstrates that there was no separation between the porous monolith and the glass tubing that could interfere with the chromatographic performance of the column. The chromatographic performance was tested as described in Example 4.

EXAMPLE 2

Preparation of a Porous Monolith and a Support in Liquid Tight Contact

A mixture was prepared according to Example 1: the nonionic surfactant Pluronic F68 (0.44 g, BASF) was dissolved in a mixture of 1.1 g water, 3.6 g methanol, 2.1 g reagent alcohol and 0.96 g HF (2.6 M). While stirring, 5.0 ml TEOS was introduced into the above solution and formed a uniform mixture.

After 5 minutes, the sol was injected into a 2.4 mm ID glass tubing. Thirty minutes later, the sol became white gels, which were then aged, dried and calcined at a temperature of about 550° C. The silica monolith inside the glass tubing had shrunk from 2.4 mm to about 2.0 mm, and was now loose within the glass tubing.

The gel and glass tubing were then subjected to heat treatment at a temperature of 850° C. After the gel cylindrical surfaces were completely sealed, the glass column was cut into 100 mm long pieces, which were over-molded using liquid crystal polymer as described in Example 1, with both ends threaded for fittings. Extra glass was then cut off and polished to a desired column length of 50 mm.

EXAMPLE 3

Preparation of a Porous Monolith and a Support in Liquid Tight Contact

The protocol according to the Example 1 was repeated, with the following difference: one end of the borosilicate glass tubing with the porous monolith inside was sealed by melting the glass at the end of the tubing only. When the glass cooled, a vacuum (about 20 inches of mercury) was applied to the open end of the tubing, and the glass tubing with the porous monolith inside was heated to a temperature at which the glass tubing softened and shrunk under the force of the outside atmospheric pressure to form a tight seal with the silica monolith inside. Use of a vacuum allowed the shrinkage to occur at a lower temperature than in the absence of the vacuum, allowing a broader range of temperatures suitable for the shrinkage step.

EXAMPLE 4

Chromatographic Performance of a Porous Monolith and a Support in Liquid Tight Contact The chromatography column prepared in Example 1 was tested for chromatographic performance to determine whether the procedure resulted in liquid tight contact between the porous monolith and the support. The column dimensions were 1.2 mm (ID)×50 mm long, the mobile phase consisted of 99% hexanes and 1% isopropyl alcohol, the flow rate was 50 µl/min, and detection was performed using UV absorbance at 254 nm. The analytes were toluene; diethyl phthalate; dimethyl phthalate. The results are shown in FIG. 4.

Figure 4:
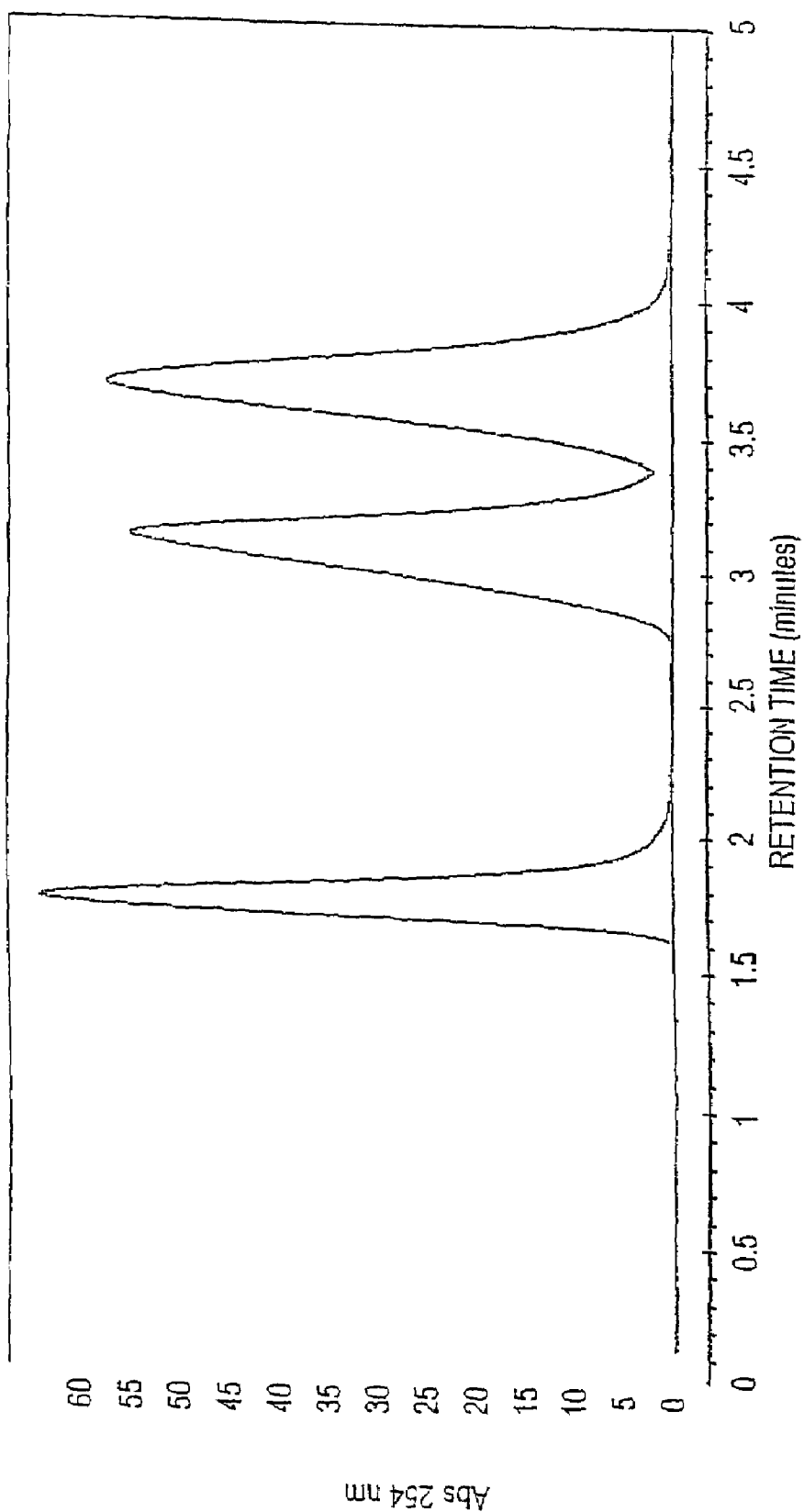
FIG. 4 shows a chromatogram demonstrating the superior separation of analytes performed by the embodiment of Example 1.

As shown in FIG. 4, the analytes are separated and show symmetrical peaks, indicating that the mobile phase flow was confined through the monolithic bed of the column, therefore there was liquid tight contact between the porous monolith and the glass tubing. If there was not liquid tight contact between the porous monolith and the glass tubing, no separation or incomplete separation would have been observed.

What is claimed is:

1. An article comprising a porous inorganic substrate contained in a support made from an inorganic material, wherein said porous substrate and support are heated to a temperature effective to shrink but not melt the support onto the porous substrate such that liquid tight contact is formed between the porous substrate and the support, wherein said temperature is near or above the softening temperature for the inorganic material, and wherein the temperature effective to shrink the support onto the porous substrate has no affect or only limited affect on the pore distribution of the porous substrate.

2. The article of claim 1, wherein the porous inorganic substrate is a porous monolith.

3. The article of claim 1, further wherein a vacuum is applied to the support that is sufficient to lower the temperature at which shrinkage occurs.

4. The article of claim 1, wherein said article is adapted for use in chromatography, catalysis, adsorption, filtration, fuel cells, optoelectronics, sensor technologies, or hydrogen storage.

5. The article of claim 1, wherein said porous inorganic substrate comprises an inorganic material or an inorganic-organic hybrid material.

6. The article of claim 5, wherein said support comprises a metal or metalloid oxide.

7. The article of claim 1, wherein inorganic porous substrate is a porous monolith formed using a sol-gel method.

8. The article of claim 1, wherein the porosity, chemistry, adsorption or catalytic characteristics of the porous substrate are modified.

9. The article of claim 8, wherein said modifying is selected from the introduction of a bonded phase, introduction of a catalytic functionality, structure remodeling, or introduction of a sensor.

10. The article of claim 1, wherein said support made from an inorganic material comprises a glass or ceramic material.

11. The article of claim 1, further comprising a protective outer layer.

12. A method of forming an article comprising a porous inorganic substrate in liquid tight contact with an inorganic support, comprising:
 a) assembling a porous inorganic substrate into a shrinkable support comprising an inorganic material, and
 b) shrinking the support onto the porous substrate by heating the article to a temperature that is effective to shrink but not melt the support onto the porous substrate, such that there is liquid tight contact between the porous substrate and the support, wherein said temperature is near or above the softening temperature for the inorganic material, and wherein the temperature effective to shrink the support onto the porous substrate has no affect or only limited affect on the pore distribution of the porous substrate.

13. The method of claim 12, wherein a vacuum is applied to the support that is sufficient to lower the temperature at which shrinkage occurs.

14. The method of claim 13, wherein said porous inorganic substrate comprises a metal or metalloid oxide selected from oxides of Si, Ge, Sn, Al, Ga, Mg, Mb, Co, Ni, Ga, Be, Y, La, Pb, V, Nb, Ti, Zr, Ta, W, Hf, or combinations thereof.

15. The method of claim 13, wherein said porous inorganic substrate is monolithic.

16. The method of claim 15, wherein said porous inorganic substrate is made using a sol-gel method.

17. The method of claim 15, wherein said porous monolith is formed from particles that are modified to form a monolith.

18. The method of claim 15, wherein said porous monolith is formed separately from said shrinkable support and inserted therein prior to shrinking.

19. The method of claim 15, wherein said porous monolith is formed inside said shrinkable support prior to shrinking.

20. The method of claim 13, wherein said shrinkable support is a glass or ceramic.

21. The article of claim 1, wherein the liquid tight contact between the porous inorganic substrate and the support is formed by a method comprising the steps of
 a) assembling the porous inorganic substrate into a support comprising an inorganic material, and
 b) shrinking the support onto the porous inorganic substrate by heating the article to a temperature that is effective to shrink but not melt the support onto the porous substrate
 wherein said temperature is near or above the softening temperature for the inorganic material, and wherein the temperature effective to shrink the support onto the porous substrate has no affect or only limited affect on the pore distribution of the porous substrate.

22. A chromatographic column comprising a porous inorganic monolith enclosed inside a glass tubing, the improvement comprising forming the porous inorganic monolith from a sol gel, calcining the porous inorganic monolith and assembling it into the glass tubing, and heating the assembly to shrink but not melt the glass tubing such that there is liquid tight contact between the porous inorganic monolith and the glass tubing wherein said heating is to near or above the softening temperature for the glass tubing, and wherein the temperature effective to shrink the glass tubing has no affect or only limited affect on the pore distribution of the porous inorganic monolith.

23. The chromatographic column of claim 22, wherein the porous inorganic monolith is formed and calcined inside the glass tubing prior to heating the assembly to shrink the glass tubing.

24. A method for separating a mixture of analytes in a sample, said method comprising the steps of
 a) providing a chromatographic column comprising a porous inorganic substrate enclosed inside a glass tubing, wherein the column has been heated to shrink but not melt the glass tubing such that a liquid tight contact is formed between the porous inorganic substrate and the glass tubing, wherein said heating is to near or above the softening temperature for the glass tubing, and wherein the temperature effective to shrink the glass tubing has no affect or only limited affect on the pore distribution of the porous inornanic substrate;
 b) applying the sample to the chromatographic column;
 c) eluting the chromatographic column with a mobile phase; and
 d) collecting the separated analytes eluting from the chromatographic column.

* * * * *